United States Patent [19]

Mahone

[11] 4,108,882

[45] Aug. 22, 1978

[54] METHOD OF PREPARING METHYLSILOXANES AND METHYLCHLORIDE

[75] Inventor: Louis G. Mahone, Midland, Mich.

[73] Assignee: Dow Corning Corporation, Midland, Mich.

[21] Appl. No.: 846,066

[22] Filed: Oct. 27, 1977

[51] Int. Cl.$^2$ ............................................. C07F 7/08
[52] U.S. Cl. ............................................ 260/448.2 E
[58] Field of Search ................................ 260/448.2 E

[56] References Cited

U.S. PATENT DOCUMENTS

| | | | |
|---|---|---|---|
| 3,432,538 | 3/1969 | Curry | 260/448.2 E |
| 3,484,468 | 12/1969 | Curry | 260/448.2 E |
| 3,576,023 | 4/1971 | Curry | 260/448.2 E |
| 3,803,195 | 4/1974 | Nitzsche et al. | 260/448.2 E |
| 4,032,557 | 6/1977 | Spörk et al. | 260/448.2 E |

*Primary Examiner*—Paul F. Shaver
*Attorney, Agent, or Firm*—Robert F. Fleming, Jr.

[57] ABSTRACT

Methylchlorosilanes are reacted in vapor phase with methyl alcohol (MeOH) in contact with a catalyst comprising a methyl pyridinium chloride or other heterocyclic aromatic methyl quaternary chloride to give the corresponding methyl siloxane and methyl chloride. This method gives extremely low yields of dimethyl ether. For example a mixture of Me$_2$SiCl$_2$ (dimethyldichlorosilane) and MeOH (methylalcohol) vapors is passed through molten methyl pyridinium chloride at 150° C to give cyclic dimethyl polysiloxanes and methyl chloride.

22 Claims, No Drawings

METHOD OF PREPARING METHYLSILOXANES AND METHYLCHLORIDE

BACKGROUND OF THE INVENTION

At present the primary commercial method for preparing methylsiloxanes is by the hydrolysis of methylchlorosilanes to give methylsiloxanes and aqueous hydrogen chloride (HCl). The latter is reacted with methyl alcohol (MeOH) silicon (Si) to give $Me_xSiCl_{4-x}$. The chlorine cycle constitutes three steps; (1) hydrolysis to give HCl; (2) reaction of HCl with MeOH to give MeCl; and (3) reaction of MeCl with Si. It would be highly desirable to reduce this to a two step process in which the chlorosilane is reacted with MeOH to give the siloxane and MeCl. Reactions of chlorosilanes with MeOH to give siloxanes are not new.

U.S. Pat. No. 3,803,195 shows the reaction of MeOH with $Me_xSiCl_{4-x}$ by a countercurrent flow method in which the column is packed with an essentially inert and acid resistant packing material. The patent states Col. 4, line 6 that catalytic agents such as Lewis-acids and cation exchange resins in the H-form may be used with the packing materials, but the use of such materials is not desirable and should be avoided. When the reaction was run with $Me_2SiCl_2$, the product was

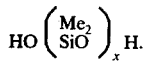

U.S. Pat. No. 2,556,897 discloses a liquid phase reaction of $Me_2SiCl_2$ with MeOH. No catalyst is suggested. The product resulting was a viscous oil.

U.S. Pat. No. 2,741,630 reacts $Me_2SiCl_2$ with MeOH at a temperature of at least 175° C in the presence of $ZnCl_2$ on silica gel. As pointed out by U.S. Pat. No. 3,803,195 use of $ZnCl_2$ promotes cleavage of Me from Si.

It is the object of this invention to provide an economical method of producing siloxanes and MeCl which involves low yields of $Me_2O$ and high yields of siloxane. Another object is to provide a method of producing primarily cyclic diorganosiloxanes and especially cyclotrisiloxanes without significant methyl cleavage.

SUMMARY OF THE PRESENT INVENTION

We have now discovered that we can obtain improved yields of alkylpolysiloxanes of the formula $R_nSiO_{(4-n)/2}$ where R is a lower alkyl radical, for instance, methyl, ethyl, propyl, etc., and $n$ is an integer from 2 to 3, that such yields can be obtained in relatively short periods of time, that the conversion of the reaction products to the useful alkyl halide which can be re-used, for instance, in making fresh alkylhalogenosilanes can be materially increased, and the amount of hydrogen halide present in the reaction zone or in the reaction mixture greatly reduced and in some respects, substantially eliminated. All these desirable results are accomplished when a known method for reacting a silane of the formula (1) $R_nSiCl_{4-n}$ with (2) MeOH to produce siloxanes of the formula $R_nSiO_{(4-n)/2}$ and MeCl in which R is an alkyl radical of 1 to 4 carbon atoms and $n$ is 2 or 3, is improved by heating a mixture of (1) and (2) in amounts of not more than a 30% mol excess of either reactant in contact with a quaternary ammonium compound catalyst selected from the group consisting (1) pyridinium chlorides of the formula

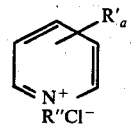

(2) compounds of the formula $R'''_4N^+Cl^-$, (3)

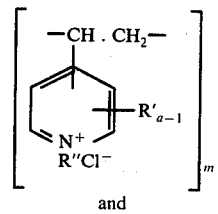

and (4)

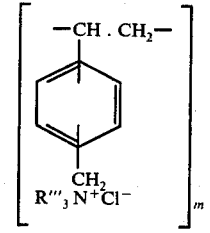

where R' is a hydrocarbon radical having 18 or less carbon atoms; "a" is an integer from 0-5; "m" is an integer greater than 1, R'' is a lower alkyl radical; and R''' is selected from the group consisting of methyl, hydroxy alkyl of 2-4 inclusive carbon atoms, aromatic hydrocarbon radicals, and $ArCH_2-$ radicals in which Ar is an aromatic hydrocarbon radical there being no more than 18 carbon atoms total in the R''' group.

DETAILED DESCRIPTION OF THE INVENTION

Among the types of radicals which may be included as the R' substituent on quaternary ammonium halide catalysts (1) and (3) in the practice of the present invention are, for instance, alkyl radicals such as methyl, ethyl, isopropyl, etc.; cycloalkyl radicals such as cyclohexyl or cyclopentyl; aliphatically unsaturated radicals such as vinyl, allyl, hexenyl, cyclopentenyl, or butadienyl; or aryl radicals such as phenyl, tolyl, benzyl, biphenyl, naphthyl, phenylmethyl, or a fused ring hydrocarbon substituent such as those found in quinoline, 3-methyl-quinoline, isoquinoline, acridine, and phenanthridine.

R''' may be the methyl radical; an aromatic radical such as phenyl, naphthyl or biphenyl; or an aromatic radical separated from nitrogen by one carbon atoms, such as the benzyl radical, R''' can also be a hydroxy alkyl radical such as β-hydroxy ethyl, β-hydroxy propyl or β-hydroxy butyl. Catalyst (3) and (4) are polymeric materials. The former can be prepared by polymerizing vinyl pyridine, or its derivatives in which R' is any of the groups shown above, and then reacting the resulting polymer with for example methyl chloride. (4) type polymers are prepared by polymerizing vinyl benzyl chloride and reacting the polymers with a tertiary amine of the formula $R'''_3N$ where R''' is any of the groups shown above. Both (3) and (4) are commercially available materials and are generally used as cationic ion exchange resins.

Said catalyst is usually present as the quaternary ammonium chloride salt, but any halide salt capable of conversion to the chloride form in situ may be employed. For example the corresponding bromide or iodide salts may be used. They will soon be converted to the chloride salt during the reaction.

It is preferred to simultaneously react the alcohol with the silane while both reactants are in the vapor phase. Any standard method of vaporization may be utilized, as for example vaporization through glass beads.

The proportions of initial reactants used are not critical. It would be obvious to one having ordinary skill in the art, however, that a reasonable excess of alcohol would be beneficial where it is desired to consume substantially all of the chloride ion. Ratios of one to one or a slight excess of silane might also be employed. Preferably the ratio of reactants ranges from 10 mol % excess of one to 10 mol % excess of the other.

The temperature at which this reaction is carried out advantageously is from about 90° C to 230° C. If temperatures below 90° C are used, the rate of the reaction may be undesirably low. The optimal temperature range is from about 120° to 180° C. This range would be the best known based upon present economical considerations. The upper temperature limit should be below that at which any undesirable decomposition of the catalyst might occur. For this reason, preferred catalysts would include ammonium quaternary compounds having substituents which do not readily participate in Hoffman type (or various other type) degradation reactions. Such an undesirable reaction could change the effective catalyst into the ineffective hydrochloride form.

The preferred pressure of this reaction is maintained at atmospheric although it may be carried out under conditions below, at or above atmospheric. Again, one skilled in the art would recognize that the pressure temperature relationship should be such that water escapes from the reaction zone. Otherwise the water formed during the reaction would accumulate to a point where the catalyst would be rendered ineffective.

This situation is to be avoided. The preferred catalyst is pyridine quaternary salt or a lower alkyl substituent thereof. This selection is based primarily upon economic factors, as currently these compositions are relatively inexpensive to obtain. Any quaternary ammonium halide salt encompassed with the claims would be sufficient, however.

Said catalyst may be employed in the solid or molten form. If the solid phase is selected, the catalyst is best absorbed upon a suitable carrier or support means. The specific carrier employed is not critical. Any known type may be used such as charcoal, diatomaceous earth or silica gel etc. The preferred carrier charcoal, for example a charcoal identified as Matheson Coleman and Bell's Darco ® brand 20 by 40 mesh. Again it is not critical to the invention what method is used to absorb the catalyst onto the support. One such acceptable method however, comprises disolution of the catalyst in water in such amounts that when the catalyst-water solution is mixed with the support, and the mixture of ingredients dried to remove substantially all of the water, there remains deposited on the support, in a homogeneous fashion, the recited amount of catalyst.

The amount of catalyst by weight in combination with the charcoal support may range widely. The upper range is limited to such quantities as would enhance the free accessibility of the catalyst to the vapors with which it must come in contact. Also economic considerations and the physical dimensions of the reactor play a key role in determining the amount of catalyst employed.

Of course, the presence of the catalyst in too low an amount may result in lower alkyl chloride conversion than is optimally obtainable with higher amounts of catalyst present. However, determining the "proper" catalytic amounts needed depends upon a variety of factors and is best determined empirically.

In carrying out this reaction, the molten catalyst or the solid form in combination with the support, are packed into a suitable reactor device which may or may not be preceded by an inactive bed of finely divide material (which acts as a volatilizing zone), for instance, finely divided glass beads, etc. Thereafter the alcohol and silane vapors are passed through the catalyst zone, maintaining at all times the desired temperature range at the reaction site.

Thereafter, the reaction products as well as the unreacted materials may be led into suitable condensing traps maintained at various temperatures designed to effect either solidification or liquification of the reaction products or reaction ingredients.

The cyclics produced in this reaction contain 18–24% by weight of $(Me_2SiO)_3$. To insure high levels of this cyclic trimer it is preferable to run the reaction at high chloride conversion (~90–99%) so as to produce dilute aqueous acid and allow isolation of the $(Me_2SiO_3)$ without significant decomposition.

It is highly significant that the cyclic trimer is a product of the reaction and exits the reactor. The ability to produce $(Me_2SiO)_3$ directly from $Me_2SiCl_2$ is a significant economic achievement. The efficient recovery of this material could be accomplished in many ways known to those skilled in the art and is not the subject of this invention. It is suggested, however, that the cyclic trimer be separated from the acid as soon as possible after condensation to prevent polymerization of the trimer due to poor isolation technique.

When the silane is trimethylchlorosilane the primary siloxane product is hexamethyldisiloxane but there may be some production of $(CH_3)_3Si\{OSi(CH_3)_2\}_x$-$OSi(CH_3)_3$ (in trace amounts based on the disiloxane produced) due to methyl cleavage. When the silane is a dialkyl dichlorosilane such as $(CH_3)_2SiCl_2$ the primary siloxane products (98%) are cyclidiorganosiloxanes of which from 18 to 25% are the cyclotrisiloxane. There may also be one to two percent of alkoxy endblocked diorganosiloxanes having on the average of 3 to 5 Si atoms and in the reactor there is a formation of a small amount of nonvolatile diorganosiloxane. This material does not deleteriously effect the reaction and can be removed from the reactor when desired. Both the nonvolatile siloxane and the methoxy endblocked siloxane are commercially useful materials.

In order that those skilled in the art may better understand how the present invention may be practiced, the following examples are given as an illustration and are not intended to serve as a limitation.

EXAMPLE 1

The apparatus, known as a liquid sparger reactor, consisted of a 1 inch diameter Pyrex ® glass column approximately 7 inches in height. 10 mililiters (10 ml) of molten catalyst were placed into said column and were supported upon a fritted glass filter located near the bottom of said column. The vaporized reactants entered the column through a 6 mm diameter glass feed tube at a point of entry below the filter support. The reactor was situated in an oil bath heated to 150° C.

The feed rate of the alcohol was controlled by a variable speed, syringe pump connected to the feed tube by 18 gage tubing. The trimethylchlorosilane was fed into the reactor by a dual syringe pump.

A 10% mol excess of alcohol over trimethylchlorosilane was provided throughout the reaction. The conditions were maintained at 150° C and atmospheric pressure.

The exit reaction products were cooled with a water condenser connected in series to the reactor. Water and unreacted hydrogen chloride and alcohol were collected in a receiver, while the volatile methyl chloride and dimethyl ether were vented into the atmosphere.

Gas chromatography was performed on the vent gas sample to determine the presence and amount of dimethyl ether produces as a contaminent, and also on the siloxane layer to determine the purity of the hexamethyldisiloxane produced. The amount of unreacted chloride was determined by acid titration of the aqueous layer. Using these analytical methods it was possible to calculate a percent methyl chloride conversion for each expermental run. An optimal chloride conversion approacing 100% is indicative of a complete reaction yielding the desired siloxanes without the unwanted hydrochloric acid by-product.

The molten catalyst salt used in this reaction was prepared by placing pyridine into a sparger reactor, and passing methyl chloride gas through the pyridine for approximately 12–18 hours at a temperature of 100° C. Thereafter the temperature was raised to 175° C to strip off or distill away any unreacted pyridine. After distillation was complete a solid residue remained which was identified as N-methyl pyridinium chloride (the methyl chloride salt of pyridine).

Trimethylchlorosilane was fed into the reactor at a rate of 170 m Eq/hr, and mixed with a 10% mol excess of vaporized methanol. These reactants were passed through the 10 mls of molten N-methyl pyridinium chloride lying at the bottom of the reactor column. Analysis of the products showed that 85.3% of the chloride ion was converted to MeCl with 550 ppm Me$_2$O in the MeCl. Gas chromatography established the production of hexamethyldisiloxane.

EXAMPLE 2

All things were the same as in Example 1, except that a second sparger reactor containing 10 mls of the molten N-methyl pyridinium chloride catalyst was connected in series with the first reactor, so that the reactants would pass through both reactors. Trimethylchlorosiloxane was fed into the reactor at an increased rate of 180 m Eq/hr maintaining the same proportional relation to the methanol as before. The chloride ion conversion increased to 97% while dimetyl ether was detected in a concentration of 430 ppm. Again the production of hexamethyldisiloxane was confirmed by gas chromatography.

EXAMPLE 3

All things were the same as in Example 1, except that a packed bed (plugged flow) reactor was placed in series with the sparger reactor described in Example 1. This second apparatus consisted of a "U" shaped tube having a ⅜" diameter and a height of 7 inches. Ten mls of charcoal containing, 10% weight N-methyl pyridinium chloride were packed into this second reactor which was likewise situated in a hot oil bath at a temperature of 150° C.

This charcoal supported catalyst was prepared in the following menner: 1 gram of N-methyl pyridium chloride was dissolved in 25 ml of water and placed in a 4 oz bottle. To this bottle was added 10 grams of charcoal (Pittsburgh PBC 12 × 20 mesh). This mixture was thoroughly shaken and thereafter left standing for about 1 hour. It was then placed into a 150° C oven until all of the water evaporated leaving the catalyst absorbed onto the surface of the charcoal.

The trimethylchlorosilane feed rate was 180 m Eq/hr. Chloride ion conversion was 92% with 360 ppm of dimethyl ether present. The hexamethyldisiloxane was confirmed by gas chromatography.

EXAMPLE 4

All things were the same as in Example 3 except 20 mols of charcoal containing 10% weight N-methyl pyridinium chloride were packed into the second reactor. The chloride ion conversion rose to 99.7% with the dimethyl ether concentration at 400 ppm. Gas chromatography confirmed the presence of hexamethyldisiloxane.

EXAMPLE 5

The apparatus was the same as that used in Example 1 except that a different molten catalyst was used. Ethyl methyl pyridine was substituted for the pyridine used in Example 1. This molten catalyst was prepared by the same method as before, however the catalyst produced was N-methyl (2-methyl 5-ethyl pyridinium) chloride (the methyl chloride salt of ethyl methyl pyridine).

The trimethylchlorosilane feed rate was 181 m Eq/hr with a 10% mole excess of methanol. Analysis showed 84% chloride ion conversion to MeCl with 380 ppm of dimethyl ether present, and gas chromatographic confirmation of hexamethyldisiloxane.

EXAMPLE 6

All things were the same as in Example 1 except N methyl (4-phenyl) pyridinium chloride was the molten catalyst. This catalyst was prepared by reacting 4-phenyl pyridine with methyl chloride under pressure at 120° C for approximately 20 hours.

The trimethyl feed rate in this reaction was 180 m Eq/hr. The chloride ion conversion as 67% while the dimethyl ether was detected at a concentration of 400 ppm. Again the product was identified as hexamethyldisiloxane.

EXAMPLE 7

All things were the same as in Example 1 except that N-methyl (quinolinium) chloride was substituted as the molten catalyst. This catalyst was purchased from an outside source.

The trimethylchlorosilane feed rate was 170 m Eq/hr. The chloride ion conversion was 70% with dimethyl ether present at a concentration of 410 ppm. Again, hexamethyldisiloxane was confirmed as the product.

EXAMPLE 8

The apparatus, catalyst and conditions used were the same as for Example 1, except dimethyldichlorosilane was substituted for the trimethylchlorosilane, and 30 mls of the molten catalyst were present in the reactor. The dimethyldichlorosilane feed rate was 392 m Eq/hr.

The conversion of chloride ion to MeCl was 76% mixed with dimethyl ether at a concentration of 300 ppm. A trace (approximately 2%) of a nonvolatile siloxane product remained in the reactor. No analysis was made of the volatile siloxane product to determine the cyclic distribution.

EXAMPLE 9

To produce a high chloride ion conversion, four sparged reactors were used in series, each reactor containing 5 mls of molten N-methyl(2-methyl 5-ethyl pyridinium) chloride salt. The dimethyl dichlorosilane was fed with syringe pumps at 191 m Eq/hr and the methyl alcohol at 420 m Eq/hr at 150° C.

A chloride ion conversion of ~99% was obtained. The $Me_2O$ in the MeCl was analyzed by GLC and found to be 450-550 ppm. The cyclic vapors were scrubbed with ~100 mls of water for 30 minutes to obtain a sample for GLC analysis.
The following cyclic distribution was obtained.

| | |
|---|---|
| $D_3$** | 23.0% |
| $D_4$ | 43.0 |
| $D_5$ | 19.2 |
| $D_6$ | 5.4 |
| $D_7$ | 0.9 |
| $D_8$ | 0.3 |
| | *91.8% |
| 1.3% $CH_3O\left[\begin{array}{c}(CH_3)_2\\SiD\end{array}\right]_x CH_3$ | |
| 93.1% where x is 3, 4, and 5 | |

A weight loss on cyclic samples always produced 100% weight loss, 30 min/150° C. This indicates there were no nonvolatile siloxanes causing GLC error. The $(Me_2SiO)_3$ was also confirmed by IR as being present in levels of 20-25%.

*GLC analysis were always ~6% low; standardized commercial cyclic preparations always analyzed at ~94% total cyclics attributable to GLC instrumentation.
**D represents the $(CH_3)_2SiO$ unit.

EXAMPLE 10

The apparatus comprised a single packed bed flow reactor. The "U" shaped column had a 9 mm inside diameter into which was placed a 50 ml volume of charcoal impregnated with 4 grams of N-methyl pyridium chloride catalyst prepared according to the method described in Example 3. A hot air oven was used to maintain the reaction zone temperature at 160° C. Trimethylchlorosilane was fed at 163.8 m Eq/hr and mixed with a 20% excess of methanol. A chloride in conversion of 99.9% was obtained with no measurable amount of dimethyl ether present. Gas chromatography identified the product as hexamethyldisiloxane.

EXAMPLE 11

All things were the same as in Example 10, except benzyltrimethylammonium chloride was substituted as the catalyst and the reaction temperature was maintained at 180° C. The chloride ion conversion was 99.6% with dimethyl ether found to be 1500 ppm. Again gas chromatography confirmed the product to be hexamethyldisiloxane.

EXAMPLE 12

A water soluble electroconductive resin salt was utilized as the catalyst in this example. Commercially available DeSoto 112 (4.8 Gm) having the general structure

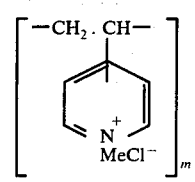

and supported on charcoal having a total volume of 60 mls, was placed into the reactor apparatus of Example 10. The temperature was maintained at 120° C. Trimethylchlorosilane was fed into the reactor at a rate of 166.2 m Eq/hr with a 20% excess of methanol. A chloride ion conversion of 99.9% resulted with a dimethyl ether concentration of 1,840 ppm. The resulting product was hexamethyldisiloxane.

EXAMPLE 13

In this example commercially available Dow ECR-34 resin having the general structure

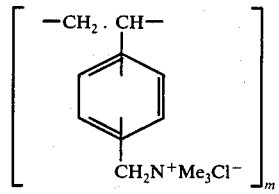

was substituted as the catalyst, and the temperature was raised to 150° C. All other conditions remained the same as in Example 12. A 98.3% chloride ion conversion was achieved. The amount of dimethyl ether produced was not recorded. Gas chromatography confirmed the product to be hexamethyldisiloxane.

EXAMPLE 14

The catalyst comprised commercially available Rohm and Haas' Amberlyst A29 resin having the structure

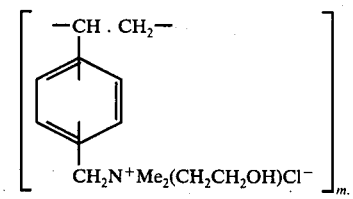

Approximately 60 ml of the catalyst in the form of resin beads were placed into the reactor (no additional support medium was needed). All other conditions were the same as in Example 13. The chloride ion conversion was 93%. The product was confirmed by gas chromatography to be hexamethyldisiloxane.

That which is claimed is:

1. In a method for reacting a silane of the formula (1) $R_nSiCl_{4-n}$ with (2) MeOH to produce siloxanes of the formula $R_nSiO_{4-n/2}$ and MeCl in which R is an alkyl radical of 1-4 carbon atoms and n is 2 or 3, the improvement comprising heating a mixture of (1) and (2) in amounts of not more than a 30% mole excess of either reactant in contact with a quaternary ammonium halide salt catalyst selected from the group consisting of (1) pyridinium chlorides of the formula

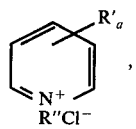

(2) compounds of the formula $R'''_4N^+Cl^-$, (3)

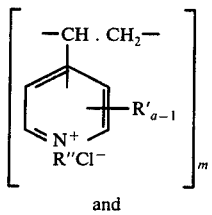

and (4)

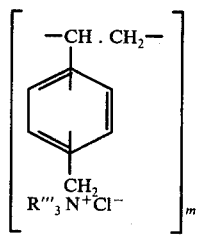

where R' is any hydrocarbon radical having 18 or less carbon atoms; a is an integer from 0-5; m is an integer greater than 1; R'' is a lower alkyl radical; and R''' is selected from the group consisting of methyl, hydroxyalkyl radicals of 2-4 inclusive carbon atoms, aromatic hydrocarbon radicals, and $ArCH_2-$ radicals in which Ar is an aromatic hydrocarbon radical, there being no more than 18 carbon atoms total in the R''' groups.

2. The method of claim 1 wherein the reactants of this reaction are present in the reaction zone in the vapor phase.

3. The method of claim 1 wherein the catalyst is present in the molten form.

4. The method of claim 3 wherein the reactants of this reaction are present in the reaction zone in the vapor phase.

5. The method of claim 1 wherein the cyclic dimethylsiloxane trimer end product is rapidly separated from acidic by-products.

6. The method of claim 2 wherein the cyclic dimethylsiloxane trimer end product is rapidly separated from acidic by-products.

7. The method of claim 3 wherein the cyclic dimethylsiloxane trimer end product is rapidly separated from acidic by-products.

8. The method of claim 4 wherein the cyclic dimethylsiloxane trimer end product is rapidly separated from acidic by-products.

9. The method of claim 1 wherein the catalyst is selected from group (1), and R'' is methyl.

10. The method of claim 9 wherein the reactants of the reaction are present in the reaction zone in the vapor phase.

11. The method of claim 9 wherein the catalyst is in molten form.

12. The method of claim 10 wherein the catalyst is in the molten form.

13. The method of claim 9 wherein the cyclic dimethylsiloxane trimer end product is rapidly separated from acidic by-products.

14. The method of claim 10 wherein the cyclic dimethylsiloxane trimer end product is rapidly separated from acidic by-products.

15. The method of claim 11 wherein the cyclic dimethylsiloxane trimer end product is rapidly separated from acidic by-products.

16. The method of claim 12 wherein the cyclic dimethylsiloxane trimer end product is rapidly separated from acidic by-products.

17. The method of claim 10 wherein the catalyst is N-methyl(2-methyl 5-ethyl pyridinium) chloride.

18. The method of claim 11 wherein the catalyst is N-methyl(2-methyl 5-ethyl pyridinium) chloride.

19. The method of claim 12 wherein the catalyst is N-methyl(2-methyl 5-ethyl pyridinium) chloride.

20. The method of claim 10 wherein the catalyst is N-methyl pyridinium chloride.

21. The method of claim 11 wherein the catalyst is N-methyl pyridinium chloride.

22. The method of claim 12 wherein the catalyst is N-methyl pyridinium chloride.

* * * * *

UNITED STATES PATENT AND TRADEMARK OFFICE
CERTIFICATE OF CORRECTION

PATENT NO. : 4,108,882
DATED : August 22, 1978
INVENTOR(S) : Louis G. Mahone

Page 1 of 2

It is certified that error appears in the above-identified patent and that said Letters Patent are hereby corrected as shown below:

In Column 2, line 58; the punctuation after the word radical should be a period not a comma.

In Column 5, line 23; the word reading "produces" should read "produced".

In Column 5, line 61; the word reading "dimetyl" should read "dimethyl".

In Column 6, line 9; the word reading "menner" should read manner".

In Column 6, line 53; the word reading "as" should read "was".

UNITED STATES PATENT AND TRADEMARK OFFICE
CERTIFICATE OF CORRECTION

PATENT NO. : 4,108,882

DATED : August 22, 1978

INVENTOR(S) : Louis G. Mahone

It is certified that error appears in the above-identified patent and that said Letters Patent are hereby corrected as shown below:

In Column 7 lines 36-38; the formula reading "$CH_3O\left[SiD^{(CH_3)_2}_3\right]_x CH_3$" should read "$CH_3O\left[SiO^{(CH_3)_2}_3\right]_x CH_3$".

Signed and Sealed this

Twenty-sixth Day of January 1982

[SEAL]

Attest:

Attesting Officer

GERALD J. MOSSINGHOFF

Commissioner of Patents and Trademarks